US010538636B2

(12) United States Patent
Pugh et al.

(10) Patent No.: US 10,538,636 B2
(45) Date of Patent: Jan. 21, 2020

(54) ROOM TEMPERATURE POLYMER CROSSLINKING USING 1-FUNCTIONALIZED BENZOCYCLOBUTENE (71) Applicants: Coleen Pugh, Akron, OH (US); Ajay Ramesh Amrutkar, Akron, OH (US)

(72) Inventors: Coleen Pugh, Akron, OH (US); Ajay Ramesh Amrutkar, Akron, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 15/728,053

(22) Filed: Oct. 9, 2017

(65) Prior Publication Data

US 2018/0030217 A1    Feb. 1, 2018

Related U.S. Application Data (62) Division of application No. 14/872,689, filed on Oct. 1, 2015, now abandoned.

(60) Provisional application No. 62/058,309, filed on Oct. 1, 2014.

(51) Int. Cl.
| | | |
|---|---|---|
| C08J 3/24 | (2006.01) |
| C08F 212/14 | (2006.01) |
| C08F 212/08 | (2006.01) |
| C07C 69/157 | (2006.01) |
| C08F 12/22 | (2006.01) |

(52) U.S. Cl.
CPC ............... *C08J 3/24* (2013.01); *C07C 69/157* (2013.01); *C08F 12/22* (2013.01); *C08F 212/08* (2013.01); *C08F 212/14* (2013.01); *C07C 2602/06* (2017.05); *C08J 2325/08* (2013.01)

(58) Field of Classification Search
CPC . C08J 3/24; C08F 12/22; C08F 212/14; C08F 212/145; C08F 20/10; C08F 220/10
See application file for complete search history.

(56) References Cited

U.S. PATENT DOCUMENTS

2015/0210793 A1* 7/2015 Park ...................... C08F 212/08
                                                               524/553

OTHER PUBLICATIONS

Kirchhoff, R.A. et al.; Benzocyclobutenes: A new Class of High Performance Polymers; J. Macromol. Sci.—Chem.; 1991; A28, 1079-1113.
Kirchhoff, R.A. et al.; Benzocyclobutenes in polymer synthesis; Prog. Polym. Sci.; 1993, 18, 85-185.
Oppolzer, W; Intramolecular Cycloaddition Reactions of ortho-Quinodimethanes in Organic Synthesis; Synthesis; 1978, 793-802.
Pugh, C et al.; Synthesis of a Polymerizable Benzocyclobutene that Undergoes Ring-Opening Isomerization at Reduced Temperature; SynLett; 2014; 25; 148-152.
Dobish, J.N. et al.; Synthesis of low-temperature benzocyclobutene cross-linker and utilization; Polym. Chem. 2012, 3, 857-860.
Jensen, F.R. et al.; Ring opening reactions of benzocyclobutene and derivatives; Tetrahedron Lett.; 1962, 15-18.
Segura, J.L. et al.; o-Quinodimethanes: Efficient Intermediates in Organic Synthesis; Chem. Rev.; 1999; 99; 3199-3246.
Chino, K. et al.; Polymerization of o-Quinodimethanes Bearing Electron-Donating Groups in Situ Formed by Thermal Isomerization of Benzocyclobutenes; Macromolecules; 1997; 30; 6715-6720.
Chino, K. et al.; Polymerization of o-quinodimethanes. III. Polymerization of o-quinodimethanes bearing electronwithdrawinggroups formed in situ by thermal ring-opening isomerization of corresponding benzocyclobutenes; J. Polym. Sci.: Part A: Polym. Chem.; 1999; 37; 1555-1563.
Choy, W. et al.; Diels-Alder reactions of .alpha.-oxy-o-xylylenes; J. Org. Chem.; 1988; 53; 5796-5798.
Garcia-Garcia, P. et al.; Competitive Pathways in the Reaction of Lithium Oxy-ortho-quinodimethanes and Fischer Alkoxy Alkynyl Carbene Complexes: Synthesis of Highly Functionalised Seven-Membered Benzocarbocycles; Chem. Eur. J.; 2011; 17; 564-571.
Fitzgerald, J.J. et al.; Reaction of Benzocyclobutene Oxides with Aldehydes: Synthesis of Peshawarine and Other 3, 4-Dihydroisocoumarins; J. Org. Chem.; 1994; 59; 4117-4121.
Shaw, S.J.; Ring-Opening of Benzocyclobutenol with Mild Bases and Trapping with Dieneophiles; Synthetic Commun.; 2007; 37; 4183-4189.
Arnold, B.J. et al.; Photochemical reactions. Part III. Thermal generation of photoenols and their derivatives from substituted 1,2-dihydrobenzocyclobutenes; J. Chem, Soc., Perkin Trans. 1; 1974; 409-414.
Denmark, S.E. et al.; Palladium- (and nickel-) catalyzed vinylation of aryl halides; Chem. Commun.; 2009; 20-33.
Jeffery, T.; Tetraalkylammonium salt-based catalyst systems for directing the arylation of vinyltrimethylsilane; Tetrahedron Lett.; 1999; 40; 1673-1676.
Lyon, C.K. et al.; A brief user's guide to single-chain nanoparticles; Polym. Chem.; 2015; 124; 8653-8660.
Harth, E. et al.; A Facile Approach to Architecturally Defined Nanoparticles via Intramolecular Chain Collapse; J. Am. Chem. Soc.; 2002; 124; 8653-8660.
Croce, T.A. et al.; Alternative o-Quinodimethane Cross-Linking Precursors for Intramolecular Chain Collapse Nanoparticles; Macromolecules; 2007; 40; 6028-6031.
Kirchhoff, R.A. et al.; Benzocyclobutenes in Polymer Synthesis; Chemtech; Sep. 1993; 22-25.

* cited by examiner

*Primary Examiner* — Roberto Rabago
(74) *Attorney, Agent, or Firm* — Renner Kenner Greive Bobak Taylor & Weber (57) ABSTRACT

Specific benzocyclobutenes serve as intramolecular or intermolecular or both intramolecular or intermolecular cross-linkers. The benzocyclobutenes can be incorporated into polymers post polymerization or can be provided as monomers that participate in homopolymerization or copolymerization with other monomer to create the polymers having benzocyclobutenes that are exploited to carry out the crosslinking. At least some of the benzocyclobutenes taught herein can be used to carry out crosslinking a ambient temperatures.

10 Claims, 5 Drawing Sheets

ROOM TEMPERATURE POLYMER CROSSLINKING USING 1-FUNCTIONALIZED BENZOCYCLOBUTENE

CROSS-REFERENCE TO RELATED APPLICATIONS

This application is a divisional application of U.S. application Ser. No. 14/872,689, abandoned, which claims the benefit of U.S. Provisional Application No. 62/058,309 filed on Oct. 1, 2014, the content of which is incorporated herein by reference.

STATEMENT REGARDING FEDERALLY SPONSORED RESEARCH OR DEVELOPMENT

This invention was made with government support under NSF DMR-1006195 awarded by National Science Foundation. The government has certain rights in the invention.

FIELD OF THE INVENTION

The present invention generally relates to particular benzocyclobutene (BCB) monomers. In some embodiments, this invention relates to the creation of homopolymers and copolymers of the benzocyclobutenes and, in further embodiments, to the subsequent crosslinking of the polymers through the use of a nucleophile. In some embodiments, BCB's are incorporated into a polymer post polymerization, and the BCBs are exploited to crosslink the polymer. In some embodiments, the present invention relates to new monomers, 1-acetoxy-4-vinylbenzocyclobutene and 1-acetoxy-5-vinylbenzocyclobutene, which are thermally stable under typical radical polymerization conditions. In some embodiments, the present invention further relates to a method for producing 1-acetoxy-4-vinylbenzocyclobutene and 1-acetoxy-5-vinylbenzocyclobutene, using a multistep synthesis that allows for the produced monomer to be (co)polymerized with other monomers through the vinyl group using radical polymerization.

BACKGROUND OF THE INVENTION

Crosslinking is one of the most widely used chemical reactions in polymer science. Linking individual polymer chains together via formation of (non)covalent bonds often imparts better mechanical properties to the polymeric material. A wide range of chemistries have been used for crosslinking purposes. These can be broadly classified as thermal stimuli based, photochemistry based, catalyst based, among others.

Benzocyclobutenes (BCBs) are one class of crosslinkers that have traditionally attracted attention because they can be thermally activated to undergo ring opening isomerization forming highly reactive intermediates that react to form C—C bonds leading to stable crosslinked structures. BCB's offer other advantages such as no formation of byproducts and no need for a catalyst. Nevertheless, the high temperature required for ring opening limits their uses in many systems. One of the drawbacks of BCBs is that they require very high temperatures (>200° C.) to undergo ring opening isomerization followed by crosslinking. These temperatures can be reduced by introducing either electron donating and/or electron withdrawing substituent at the benzylic carbon(s). Harth and coworkers have reported a BCB-based crosslinker that undergoes ring opening at a lower temperature but their approach is based on post-polymerization attachment of a crosslinker to the polymer backbone, while at least some embodiments of the invention disclosed herein provide for direct incorporation of BCB-based crosslinker into the polymer during polymerization. Harth, E. et. al., *Polym. Chem.* 2012, 3, 857-860.

Figure 1:
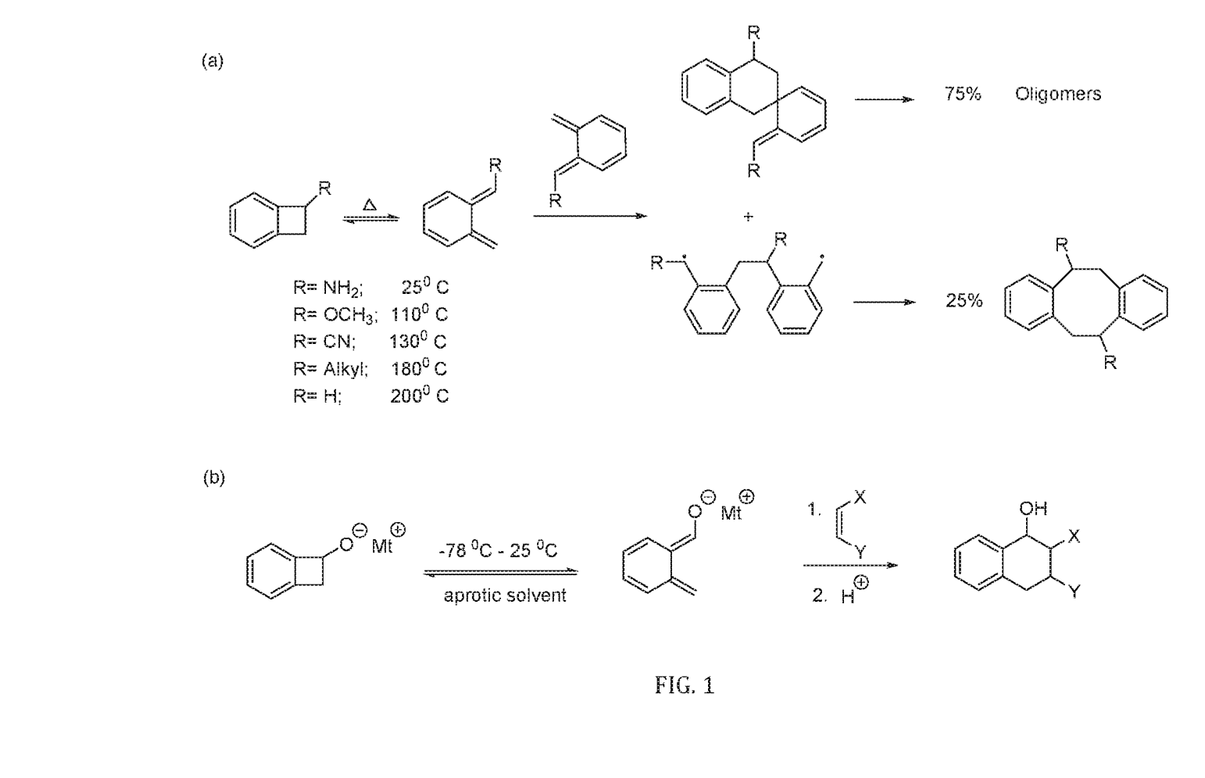
FIG. 1 provides reaction schemes for comparison, with reaction scheme (a) therein showing thermal ring opening isomerization of 1-substituted BCBs to form corresponding oQDMs and subsequent products, and reaction scheme (b) showing ring opening of BCB at lower temperature using alkoxide anion substituent to form corresponding oQDM and its subsequent trapping by a dienophile.

Benzocyclobutene (BCB), a bicyclic compound with a 4-membered ring, has been widely used for its ability to undergo thermal ring opening isomerization to form a highly reactive intermediate, o-quinodimethane (oQDM). In the presence of a dienophile it undergoes cycloaddition reaction to form the corresponding cycloadduct whereas in the absence of a dienophile reacts irreversibly with itself forming dibenzocyclooctadiene or oligomeric structures containing C—C bonds. This is shown in FIG. 1, reaction scheme (a), which shows thermal ring opening isomerization of 1-substituted BCBs to form corresponding oQDMs and subsequent products. Temperatures mentioned for various substituents are approximate temperatures based on literature; such as: Oppolzer, W. *Synthesis* 1978, 793-802; Chino, K. et al.; *Macromolecules* 1997, 30, 6715-6720; and Chino, K. et al.; *J. Polym. Sci.: Part A: Polym. Chem.* 1999, 37, 1555-1563.

Choy and coworkers have reported a BCB with alkoxide anion as substituent on the benzylic carbon that undergoes ring opening and cycloaddition reactions with dienophiles at temperatures as low as −78° C.-0° C., as shown in FIG. 1, reaction scheme (b). Choy, W.; Yang, H., "Diels-Alder Reactions of α-oxy-o-xylylenes", J. Org. Chem. 1988, 53, 5796-5798. This accelerated ring opening of BCBs using anions has been rarely used in organic chemistry, and has not been used in polymer chemistry. Choy, W.; Yang, H., "Diels-Alder Reactions of α-oxy-o-xylylenes", J. Org. Chem. 1988, 53, 5796-5798. Shaw, S. J., "Ring-Opening of Benzocyclobutenol with Mild Bases and Trapping with Dienophiles", Synthetic Commun. 2007, 37, 4183-4189. There is a need in the art for BCBs giving access to polymers that can be crosslinked at ambient or even sub-ambient temperatures. Herein, ambient or room temperature is to be understood as being from 60 to 95° F. (15.5 to 35° C.).

The ring opening isomerization of BCB to oQDM is a temperature dependent equilibrium, i.e., at any given temperature, there will be a distribution of unreacted BCBs and products formed from reacted BCBs at that temperature. As the temperature increases, half-life of oQDM decreases leading to faster and higher consumption of BCBs to form cycloadducts. This temperature-dependent equilibrium of BCBs can be useful in controlling the crosslinking of BCB-containing polymers. For example, a BCB-containing polymer could be crosslinked slower at lower temperature or could be crosslinked faster at higher temperature. This ring opening temperature can be lowered by substituting one or more benzylic positions of a BCB by a substituent. Both the electron donating as well as withdrawing groups have been shown to lower the ring opening isomerization temperature. Segura, J. L.; Martin, N., "O-quinodimethanes: Efficient Intermediates in Organic Synthesis", Chem. Rev. 1999, 99, 3199-3246. The effect of a substituent in lowering the ring opening isomerization is noticeable even in the case of mono-substituted BCBs (1-substituted BCBs) as shown in FIG. 1, scheme (a). It is worth noting that the temperature dependent equilibrium is also valid in the case of 1-substituted BCBs thereby availing the ability to control crosslinking parameters in 1-substituted BCB containing polymers. Oppolzer, W. *Synthesis* 1978, 793-802, has reported the approximate reaction temperatures (for 18 hour reactions) for various 1-substituted BCBs, whereas Chino, K. et al.;

*Macromolecules* 1997, 30, 6715-6720 and Chino, K. et al.; *J. Polym. Sci.: Part A: Polym. Chem.* 1999, 37, 1555-1563 has reported examples of electron donating and electron withdrawing group as a substituents.

Though thermal activation of BCBs for the formation of crosslinked material has gained wide attention in the polymer field, chemical activation of BCBs has remained neglected. It has been rarely used in organic chemistry for the synthesis of intermediates. This disclosure reports the synthesis of a new, polymerizable, BCB-based crosslinkers having thermally stable 4-membered ring yet the copolymer containing this BCB can be chemically activated to undergo rapid crosslinking at room temperature using a suitable nucleophile. In some embodiments, this rapid crosslinking at room temperature has been utilized to make single chain polymer nanoparticles via intramolecular chain collapse utilizing what is termed herein a pseudo-high dilution continuous addition method.

SUMMARY OF THE INVENTION

In a first embodiment, the present invention provides a benzocyclobutene monomer according to the following formula:

wherein R1 is selected from the group consisting of:

wherein n is 0 or more; or R1 is non-existent, or wherein Z is any linkage between the norbornene and the benzene ring; wherein R2 is selected from CH3, aliphatic groups, cycloaliphatic groups, and aromatic groups, and wherein A is either non-existent or is selected from any structural unit that is incapable of reacting with a nucleophile.

In a second embodiment, the present invention provides a monomer as any of the forgoing embodiments, having the formula:

In a third embodiment, the present invention provides a method of forming a copolymer comprising the steps of:
copolymerizing a first monomer and a second monomer, the second monomer being selected according to the following chemical formula:

wherein R1 is selected from the group consisting of:

wherein n is 0 or more; or R1 is non-existent, or wherein Z is any linkage between the norbornene and the benzene ring; wherein R2 is selected from CH3, aliphatic groups, cycloaliphatic groups, and aromatic groups, and wherein A is either non-existent or is selected from any structural unit that is incapable of reacting with a nucleophile.

In a fourth embodiment, the present invention provides a method as in the third embodiment, wherein the first monomer is selected from the group consisting of styrene, acrylates, methacrylates, acrylamides, methacrylamides, cyclopentenes, norbornenes, and cyclooctadienes.

In a fifth embodiment, the present invention provides a method as in any of the third through fourth embodiments, wherein R1 is $CH_2=CH$, and copolymerization is carried out through radical polymerization.

In a sixth embodiment, the present invention provides a method as in any of the third through fifth embodiments, wherein R1 is:

and copolymerization is carried out through radical polymerization.

In a seventh embodiment, the present invention provides a method as in any of the third through sixth embodiments, wherein R1 is and copolymerization is carried out through radical polymerization.

In an eighth embodiment, the present invention provides a method as in any of the third through seventh embodiments, wherein R1 is and copolymerization is carried out through ring-opening metathesis.

In a ninth embodiment, the present invention provides a method as in any of the third through eighth embodiments, wherein the method further includes crosslinking the resultant copolymer of said step of copolymerizing.

In an tenth embodiment, the present invention provides a method as in any of the third through ninth embodiments, wherein said step of crosslinking occurs in the presence of a nucleophile, wherein the nucleophile is selected from the group consisting of BuLi, sec-BuLi, NaOMe, nBuNa, and LiOMe.

In an eleventh embodiment, the present invention provides a method as in any of the third through tenth embodiments, wherein the crosslinking is intermolecular crosslinking.

In a twelfth embodiment, the present invention provides a method as in any of the third through eleventh embodiments, wherein the crosslinking is intramolecular crosslinking.

DETAILED DESCRIPTION OF ILLUSTRATIVE EMBODIMENTS

In some embodiments, the present invention provides benzocyclobutene monomers in accordance with the following chemical formula:

wherein R2 is selected from CH3, aliphatic groups, cycloaliphatic groups, and aromatic groups and wherein Z is any linkage between the norbornene and the benzene ring. In some embodiments, Z can be virtually any structural element. In some embodiments, Z is selected from n-alkyl, branched alkyl, cycloaliphatic alkyl, ether, amide, fluorocarbon, and siloxane units.

In some embodiments, the present invention provides benzocyclobutene monomers in accordance with the following chemical formula:

wherein R2 is selected from CH3, aliphatic groups, cycloaliphatic groups, and aromatic groups.

In some embodiments, the present invention provides benzocyclobutene monomers in accordance with the following chemical formula:

wherein R1 is selected from the group consisting of:

wherein n is 0 or more; or R1 is non-existent, or wherein Z is any linkage between the norbornene and the benzene ring; wherein R2 is selected from CH3, aliphatic groups, cycloaliphatic groups, and aromatic groups, and wherein A is either non-existent or is selected from any structural unit that is incapable of reacting with a nucleophile.

In some embodiments, the aliphatic groups, cycloaliphatic groups, and aromatic groups of R2 may be modified with any structural unit. In some embodiments, the structural unit may be selected from n-alkyl, branched alkyl, cycloaliphatic alkyl, ether, amide, fluorocarbon, alcohol, fluorine, and siloxane units.

In some embodiments, Z can be virtually any structural element. In some embodiments, Z is selected from n-alkyl, branched alkyl, cycloaliphatic alkyl, ether, amide, fluorocarbon, and siloxane units.

Figure 2:
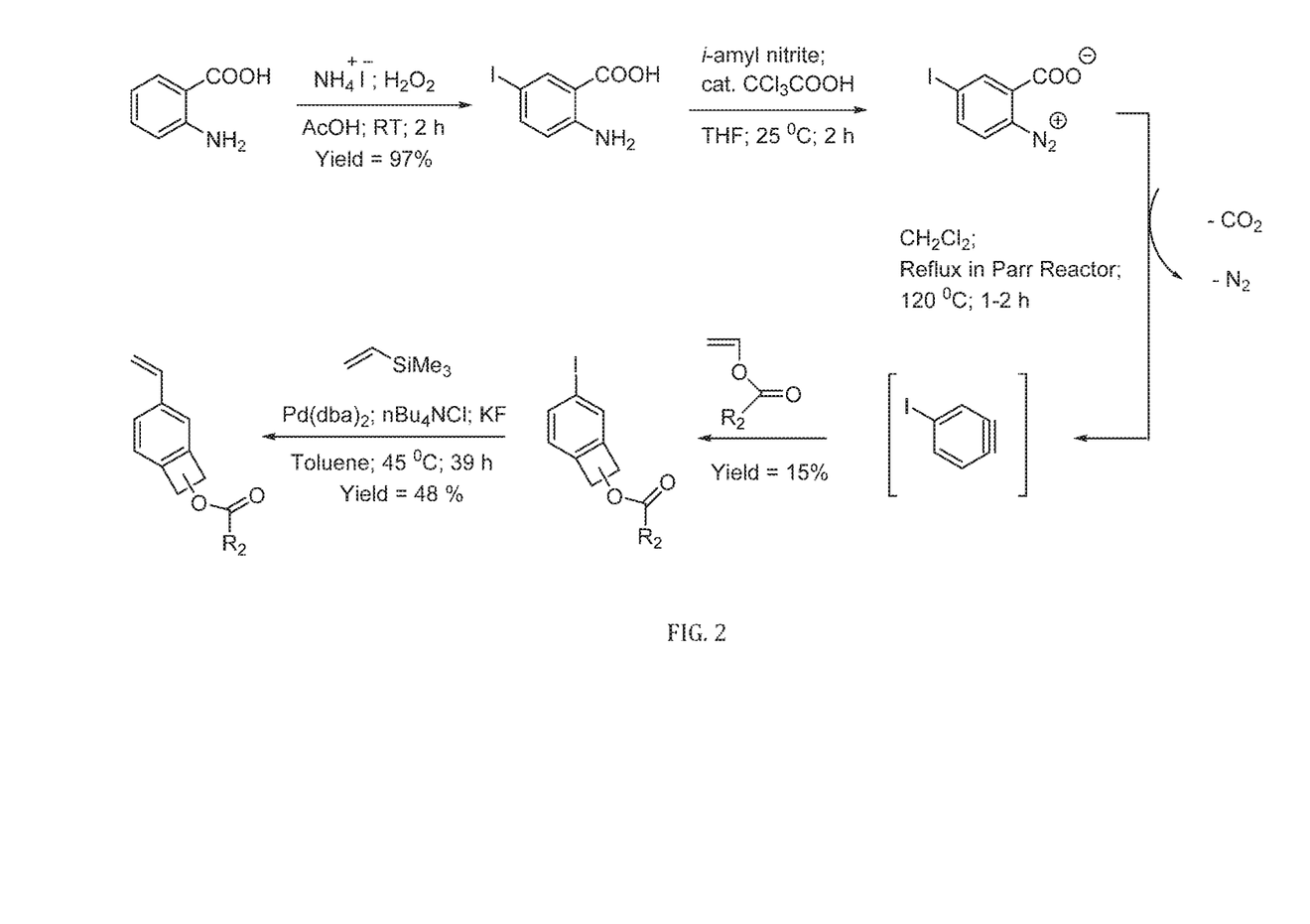
FIG. 2 provides the reaction scheme for the synthesis of new BCB monomer/crosslinkers in accordance with this invention.

In some embodiments, R1 is $CH_2=CH$ and R2 is $CH3$ forming co-1-acetoxy-4/5-vinylbenzocyclobutene, wherein the use of "co" and "4/5" is to be understood and indicating that a mixture of BCB monomers is created with some having vinyl at the 4-position and some having vinyl at the 5-position, i.e., a mix of 1-acetoxy-4-vinylbenzocyclobutene and 1-acetoxy-5-vinylbenzocyclobutene. The general chemical formula is provided below:

In some embodiments, as shown in FIG. 2, the monomers in accordance with this invention are synthesized via multistep synthesis starting with regioselective halogenation of commercially available anthranilic acid. The formed iodoanthranilic acid was then reacted under diazotization reaction conditions to make iodo-benzenediazonium carboxylate salt which was thermally decomposed to produce iodobenzyne. This highly reactive intermediate, iodobenzyne, was trapped in situ with vinyl acetate via [2+2] cycloaddition to produce a mixture of regioisomers of iodo-1-acetoxy benzocyclobutene (a mixture of 1-acetoxy-4-iodoBCB and 1-acetoxy-5-iodoBCB, or, per the nomenclature introduced above, 1-acetoxy-4/5-iodoBCB). The polymerizable styrenic derivate of this compound was prepared by introducing vinyl group onto the aromatic ring employing transition metal-catalyzed cross-coupling reactions. Modified Heck coupling reaction conditions that employ vinyl trimethyl silane as the vinyl source and use n-tetrabutyl ammonium chloride as the phase transfer agent were used to obtain a mixture of 1-acetoxy-4-vinylBCB and 1-acetoxy-5-vinylBCB in 48% yield for the final step.

Figure 3:
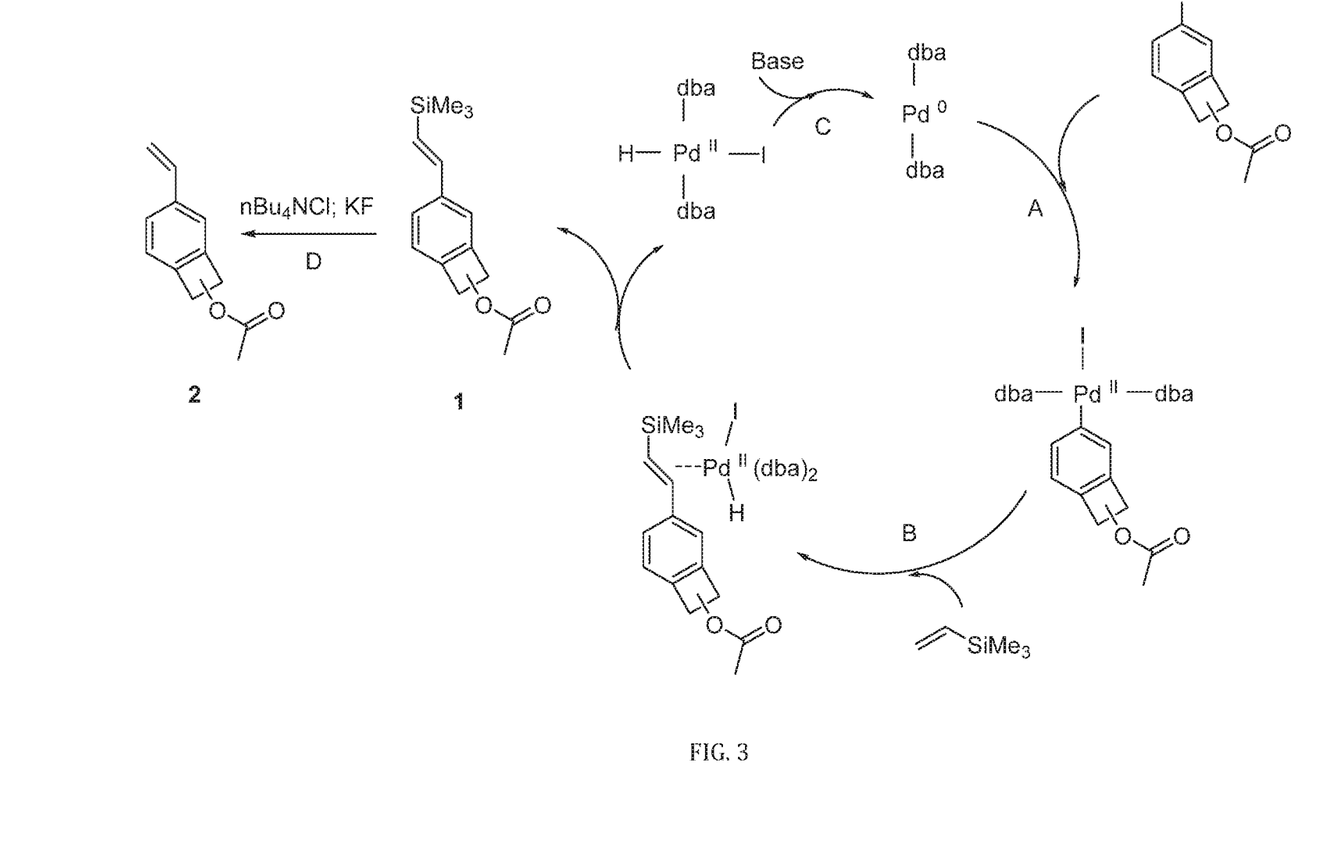
FIG. 3 shows the specifics of a Heck Coupling step of FIG. 2 and specifically shows the creation of co-1-acetoxy-4/5-vinylBCB via a multistep organic transformation starting from anthranilic acid.

The specifics of an exemplary Heck coupling are provided in FIG. 3. The polymerizable styrenic derivate of 1-acetoxy-4-iodoBCB and/or 1-acetoxy-5-iodoBCB was prepared by introducing vinyl group onto the aromatic ring employing modified heck coupling reaction conditions. In the first step, 1-acetoxy-4-iodoBCB and/or 1-acetoxy-5-iodoBCB reacts with Pd(dba)2 complex via oxidative addition to form the corresponding Pd(II) intermediate (Path A). This intermediate then reacts with vinyl trimethylsilane by insertion which is then followed by β-hydrogen elimination to form the intermediate complex (Path B). This complex then dissociates to form the silylated product (Compound 1) and Pd(II) complex. Pd(II) complex is converted back to active Pd(0) with the help of base (Path C). The silylated product (Compound 1) further reacts with fluoride source (KF) and gets deprotected to form the desired vinylated product (Compound 2). Compound 1 is never isolated, but is formed in the reaction sequence. Deprotection of Compound 1 occurs in one pot fashion to obtain Compound 2. In the reaction, n-tetrabutyl ammonium chloride serves as phase transfer agent and KF serves as base as well as fluoride source.

The polymerizable acrylate derivative of the 1-acetoxy-4-iodoBCB and/or 1-acetoxy-5-iodoBCB compound is prepared by introducing acrylate group onto the aromatic ring employing techniques that will be discernable by those of ordinary skill in the art, based on organic chemistry principles and research of reaction chemistries and coupling techniques. The polymerizable methacrylate derivative of the 1-acetoxy-4-iodoBCB and/or 1-acetoxy-5-iodoBCB compound is prepared by introducing methacrylate group onto the aromatic ring employing techniques that will be discernable by those of ordinary skill in the art, based on organic chemistry principles and research of reaction chemistries and coupling techniques. The polymerizable norbornene derivative of the 1-acetoxy-4-iodoBCB and/or 1-acetoxy-5-iodoBCB compound is prepared by introducing acrylate group onto the aromatic ring employing techniques that will be discernable by those of ordinary skill in the art, based on organic chemistry principles and research of reaction chemistries and coupling techniques.

The acetoxy or ester of 1-hydroxyBCB at the cyclobutene serves as a protecting group for the BCB, making it thermally stable under standard polymerization conditions so that the vinyl end group can be exploited to homopolymerize the BCB or copolymerize the BCB with one or more additional monomers without premature ring opening of the 4-membered butene ring. The BCB of the resultant homopolymer or copolymer can be deprotected using a nucleophile to form a desired alkoxide anion that provides crosslinking. In some embodiments, the crosslinking is intermolecular. In some embodiments the crosslinking is both intermolecular and intramolecular. In other embodiments, a single copolymer chain is crosslinked via selective intramolecular crosslinking forming (non)covalent bonds between the units of same chain, thus forming nanoparticles.

When R1 is chosen to be the alkene or acrylate or methacrylate disclosed above, the monomer can be copolymerized through either ionic or radical polymerization with virtually any other monomer capable of participating in such polymerization. In some embodiments, radical polymerization is used because anionic polymerization, which involves use of a highly nucleophilic carbanion initiator, can potentially deprotect 1-acetoxyBCB and prematurely consume the crosslinker, while cationic polymerization often requires use of stringent reaction conditions (such as much lower temperature, inert atmosphere, etc.) and is often not easily implemented. Radical polymerization on the other hand offers broader functional group tolerance, and accessible reaction conditions that can be used with readily available resources.

Controlled radical polymerization techniques such as atom transfer radical polymerization (ATRP), reversible addition fragmentation transfer (RAFT) and nitroxide-mediated radical polymerization (NMP) provide access to polymers with controlled molecular weights and narrow molecular weight distribution. ATRP, which typically employs a transition metal catalyst-ligand system and relies on the reversible activation and deactivation of a polymer chain facilitated by transition metal-ligand complex, has been extensively used among the other options. ATRP employing Cu-based catalyst system is widely used among other transition metals. It also offers ability to perform chain extension of the macro-initiator to make diblock/triblock copolymers without worrying about the homopolymer impurities of the second block as is the case with RAFT.

In some embodiments, the comonomers for radical polymerization may be selected from styrene, acrylates, methacrylates, acrylamides, and methacrylamides.

When R1 is chosen to be the nobornene disclosed above, the monomer can be copolymerized through ring-opening metathesis with virtually any other monomer capable of participating in such polymerization. In some embodiments the comonomers for ring-opening metathesis are selected from the group consisting of cyclopentene, norbornene, cyclooctadiene, and their respective derivatives.

In some embodiments, the present invention provides polymers containing 1-acetoxyBCB or an ester of 1-hydroxyBCB, wherein the 1-acetoxyBCB or ester of 1-hydroxyBCB can ultimately be employed to crosslink the polymer either intermolecularly to other such polymers or intramolecularly to itself. The polymer broadly has the following structure:

wherein n and m are greater than 0, wherein "monomer" represents any appropriate monomer in accordance with the teaching herein (i.e., being dependent on the type of polymerization employed), and wherein the connection between the benzene ring and the polymer backbone is represented by an indeterminate bond (wavy line) because it represents various types of couplings in accordance with the monomer employed, particularly the R1 group. Additionally, this is to represent that, in some embodiments, the BCB can be bound to a polymer after the polymerization of the polymer. Thus, while some embodiments are directed to incorporation of the BCB into a polymer backbone during polymerization by exploiting a group (such as vinyl) that facilitates polymerization, other embodiments allow that a homopolymer or copolymer can first be formed and then modified with the BCBs of this invention.

In some embodiments, the polymer has the following formula

The resultant copolymers can be crosslinked in the presence of a nucleophile. In some embodiments, the nucleophile is selected from the group consisting of BuLi, NaOMe, nBuNa, sec-BuLi, and LiOMe. The polymer and the nucleophile are combined in solvent, and the nucleophile deprotects the ester group of the BCB monomer, creating a alkoxide that reacts with another alkoxide created on either the same polymer (intramolecular) or a separate polymer to form crosslinking.

A detailed description of experiments leading to the provision of the above disclosure follows in the Examples section below.

EXAMPLES

Introduction

Prior work reported the synthesis of a new monomer based on 1-functionalized vinyl BCB that contains a vinyl group on the aromatic ring and a substituent on the benzylic position. See Pugh, C.; Baker, J. S.; Storms, W. K. *SynLett* 2014, 25, 148-152, "Synthesis of a Polymerizable Benzocyclobutene that Undergoes Ring-Opening Isomerization at Reduced Temperature." This monomer could advantageously be incorporated into a polymer backbone via the vinyl group and could be crosslinked post-polymerization using the BCB group. However the temperature for crosslinking was in the range of from 100-150° C., and lower crosslinking temperatures would be preferred. Thus, a specific embodiment of this invention provides a new, ambient temperature crosslinker on the same lines; ideally making co-1-alkoxide-4/5-vinylBCB. However, it was found the higher reactivity of 1-alkoxideBCB towards dienophiles at lower temperatures would make co-1-alkoxide-4/5-vinylBCB highly unstable and difficult to incorporate in the polymer backbone selectively via vinyl group polymerization. To overcome this, the present invention employs a protecting group for the alkoxide substituent.

An ideal protecting group makes the resulting BCB: (1) thermally stable under standard polymerization conditions so that vinyl BCB can be incorporated without premature ring opening of the 4-membered ring, (2) chemically stable under one of the chain polymerization mechanisms used for polymerization of vinyl monomer (such as radical or ionic polymerization) and (3) easy to deprotect to form an alkoxide anion at ambient temperatures which in turn would form the desired crosslinks. Two protecting groups were proposed—proton and ester protecting groups—which form 1-hydroxyBCB and 1-acetoxyBCB respectively. (Choy, W.; Yang, H. *J. Org. Chem.* 1988, 53, 5796-5798; and Shaw, S. J. *Synthetic Commun.* 2007, 37, 4183-4189) These two compounds were formulated per available literature, and tested for their thermal stability (Wasserman, H. H.; Solodar, J. J. Am. Chem. Soc. 1965, 17, 4002-4003; and Chino, K.; Takata, T.; Endo, T. Macromolecules 1997, 22, 6715-6720).

Room temperature in the following experiment can range from 15.5 to 35° C., the experiments being performed in environments maintained between such ranges, and the room temperature was not necessarily definitively measured.

Testing of 1-hydroxyBCB

A stock solution of 1-hydroxyBCB (50 mg, 0.42 mmol) with 1,1,1,2-tetrachloroethane (35 mg, 0.21 mmol) as internal standard in 3 ml of DMSO-d6 was prepared. This solution was then split into 3 NMR tubes equally and each of the tubes was heated at different temperatures for various time intervals. Decomposition of 1-hydroxyBCB was monitored via loss of methylene proton resonances of 1-hydroxyBCB as compared to internal standard. 1-hydroxyBCB is reported to mainly undergo thermal rearrangement to o-tolualdehyde but some side reactions are also possible. NMR data at 60° C. and at initiation (0 hours) and at 24 hours showed that more than 60% of 1-hydroxyBCB was consumed in 24 hours at 60° C. indicating its thermal instability. 1-hydroxyBCB is known to undergo thermal decomposition (mainly via rearrangement to o-tolualdehyde) over a period of time. In fact, NMR-Temperature experiments of the present inventors showed that 60% of 1-hydroxyBCB underwent thermal decomposition at 60° C. in 24 hours, Table 1.

TABLE 1

| Thermal Decomposition 1-hydroxyBCB | | |
|---|---|---|
| Temperature (° C.) | % 1-hydroxyBCB consumed | % o-tolualdehyde formed |
| 60 | 61% | 26% |
| 80 | 85% | 47% |

This puts restriction on the polymerization temperature that can be used with 1-hydroxyBCB.

Testing of 1-acetoxyBCB

On the other hand, using NMR-Temperature experiments, it was found that 1-acetoxyBCB is thermally stable for at least 48 hours at 100° C. A 10 mol % solution of 1-acetoxyBCB in bromopentafluorobenzene with 5 mol % 1,1,1,2-tetrachloroethane as internal standard was heated to different temperatures. Concentration of BCB can affect the rate at which it is consumed because, the higher the concentration, the higher is the probability for the ring opened isomer to undergo dimerization. 10 mol % solution in fluorinated solvent was used to mimic the possible polymerization conditions for the preparation of poly(pentafluorostyrene-co-1-acetoxy-4/5-vinylBCB) with 90:10 as the comonomer feed ratio. Any other solvent with boiling point higher than 100° C. can be used for this NMR-Temperature study. Aliquots were taken at different time intervals such as, 0 hours, 24 hours and 48 hours and analyzed by NMR spectroscopy. The loss of benzylic methine proton in 1-acetoxyBCB (labeled as Hb in Table 2) was monitored by comparing the integration of benzylic methine proton to the integration of internal standard. For reference stacked NMR spectra of aliquots were taken at different times at 100° C. and showed no change in the integration of methine proton, indicating that the 4-membered ring with acetate group is stable for at least 48 hours at 100° C. All the values of %1-acetoxyBCB consumed are within the range of experimental errors and also no new resonances were seen in any of the samples.

TABLE 2

Thermal decomposition of 1-acetoxyBCB (10 mol% solution in bromopentafluorobenzene with 5 mol% 1,1,1,2-tetrachloroethane as internal standard) as monitored using $^1$H NMR spectroscopy using methine proton resonances of 1-acetoxyBCB and methylene protons of internal standard at different temperatures and various time intervals

| Temperature (° C.) | Time (h) | % 1-acetoxyBCB consumed |
|---|---|---|
| 60 | 24 | 1.2% |
| 60 | 48 | −12% |
| 80 | 24 | 1% |
| 80 | 48 | 2.5% |
| 100 | 24 | −1% |
| 100 | 48 | 1% |

This is stable enough to prepare (co)polymers using chain polymerization mechanisms such as radical polymerization.

Figure 4:
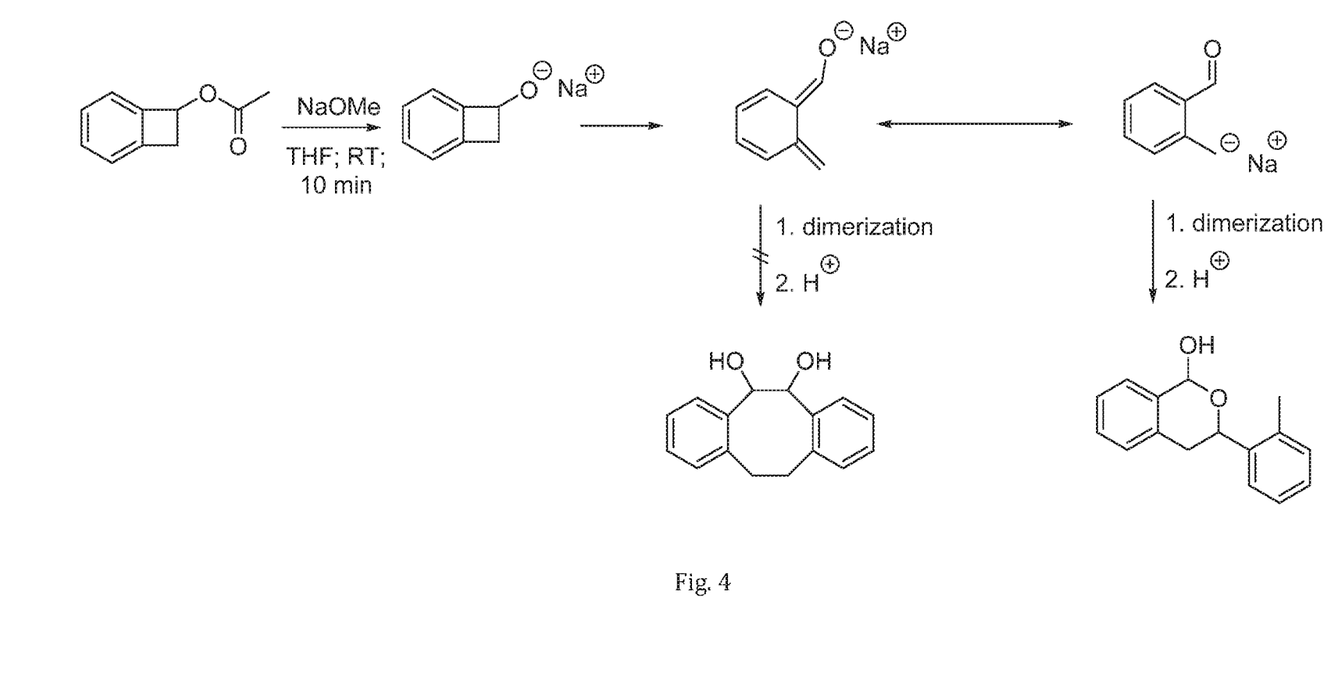
FIG. 4 shows the deprotection of 1-acetoxyBCB using NaOMe.

1-acetoxyBCB can be deprotected using a nucleophile to obtain the desired alkoxide BCB. It is interesting to note that upon alkoxide oQDM formation, it does not dimerize to give dibenzocyclooctadiene-type structures and oligomers. Due to the presence of alkoxide anion, it has one more resonance structure, o-formylbenzhydryl anion. It is this resonance structure that dimerizes to form lactol-type structures rather than oQDM dimerizing with each other, as seen in FIG. 4. This behavior is in stark contrast to the typical thermal ring opening of other substituted-BCBs which leads to the formation of oQDMs which dimerize further.

Deprotection of 1-acetoxyBCB Using NaOMe at Room Temperature and Characterization of Products To check the feasibility of ester deprotection, we treated THF solution of 1-acetoxyBCB with NaOMe at room temperature. NaOMe solution in MeOH (25 wt % in MeOH) (270 mg, 1.24 mmol) was added at once to 1 mL THF solution of 1-acetoxyBCB (100 mg, 0.62 mmol) under nitrogen atmosphere at room temperature. On addition of NaOMe, color of the contents changed instantaneously from light yellow to dark orange and the flask became warm. After 10 minutes, contents were quenched with 1 mL of saturated aqueous NH4Cl and transferred to a separating funnel. Organic phase was extracted using 6 mL of Et2O (2 mL each 3 times). All the organic phases were combined, dried over MgSO4 and concentrated on rotary evaporator. Hexanes solution of the crude was stored in fridge overnight that precipitated to give white crystals. 1H and 13C NMR showed lactone version of the product.

Instantaneous color change of the solution was observed upon addition of NaOMe, suggesting instant deprotection of the acetate group to form alkoxide followed by its dimerization at room temperature. We were able to isolate the lactone type structure as was obtained previously in the literature using other routes. Unlike other substituted BCBs, 1-acetoxyBCB has been proposed to undergo decomposition to benzocyclobutadiene and acetic acid at temperatures in excess of 120° C. based on the DSC study though no characterization of the resulting products by techniques such as NMR, HPLC is reported. (Chino, K. et al.; *Macromolecules* 1997, 30, 6715-6720).

The model experiment studies mentioned above on 1-acetoxyBCB led us to determine that acetate protecting group is the suitable protecting group and can serve as the latent precursor to the formation of alkoxide BCB. It also suggested that it is possible to incorporate BCBs in the polymer that are capable of forming alkoxide anion and undergo subsequent crosslinking at room temperature. 1-acetoxy-4/5-vinylBCB was then designed as the monomer/crosslinker that can be incorporated in the polymer backbone through vinyl group, wherein the acetate group can then be deprotected using a nucleophile at room temperature to form the desired crosslinks.

Synthetic Route for the Synthesis of 1-functionalized vinylBCBs

In order to prepare a new monomer/crosslinker that can be incorporated in the polymer backbone, we utilized a synthetic route for the synthesis of 1-functionalized vinylBCBs. Per FIG. 2, we first regioselectively halogenated anthranilic acid to obtain iodo anthranilic acid, which on subsequent diazotization produced the corresponding iodobenzene diazonium carboxylate salt.

In a 600 mL beaker with a stir bar, anthranilic acid (20.4 gms, 146 mmol) and ammonium iodide (22 gms, 153.4 mmol) were dissolved in 100 mL glacial acetic acid and cooled in ice bath for 10 minutes. To this cooled solution, hydrogen peroxide (35% w/w in H2O) (14.96 gms of aqueous solution, 153.4 mmol) was added batchwise over 10 minutes and stirred in ince bath for further 30 minutes. Contents removed from ice bath and stirred at room temperature for 90 minutes after which they had turned into slurry of precipitated tan-colored powder suspended in the solvent. The precipitate was filtered over glass frit, washed with plenty of water until the filtrate was colorless. Contents on the frit were dried in vacuum oven overnight at 80° C. to obtain tan-colored powder with m.p.=218° C.-220° C. % Yield=96.9%.

This salt was heated to form benzyne which was trapped in situ via [2+2]cycloaddition with vinyl acetate to obtain a mixture of regioisomers of co-1-acetoxy-4/5-iodoBCB, as per FIG. 2. In a beaker with a stir bar, iodo anthranilic acid (10 gms, 38.02 mmol) and trichloroacetic acid (63 mg, 0.38 mmol) were dissolved in 50 mL THF and stirred in ice bath for 10 minutes. To the cooled solution, iso-amyl nitrite (5.6 gms, 47.53 mmol) was added batch wise over 15 minutes. On complete addition contents had turned orange in color and further stirred in ice bath for 30 minutes. Beaker as taken out of ice bath and stirred at room temperature for 90 minutes after which contents had turned into dark grey precipitate suspended in the solvent. The precipitate, iodo benzene diazonium carboxylate salt, was filtered over glass frit and washed with dichloromethane to displace THF till the filtrate is colorless. The slurry of iodo benzene diazonium carboxylate salt in dichloromethane was transferred to a parr reactor containing vinyl acetate (20 gms, 228 mmol). Parr reactor was immersed in oil bath preheated to 120° C. heated for 2 hours after which heating was stopped and contents cooled down to room temperature overnight. Contents from parr reactor were then concentrated to remove excess of solvent and vinyl acetate. The crude obtained was then dissolved in 15 mL of acetone and added batchwise to a refluxing mixture of 13 gms of silica gel and 100 mL of hexanes to boil off acetone and precipitate impurities. The slurry obtained was then filtered over glass frit, solids disposed and filtrate reduced on rotovap. The crude obtained was purified by column chromatography using 80:20 (hexanes: diethyl ether) as eluent system to obtain dark orange colored oil (Rf=0.35) as the product. Total weight=1.694 gms (% Yield=15.5%).

The polymerizable styrenic derivate of this compound was prepared by introducing vinyl group onto the aromatic ring employing transition metal-catalyzed cross-coupling reactions. Aryl iodide has nucleophile-sensitive group on it since in our model compound studies we observed that NaOMe completely deprotected acetate group instantaneously at room temperature. This nucleophile-sensitivity restricted the choice of cross-coupling reaction that could be used. Typical options available for transition metal-catalyzed C—C bond forming cross-coupling reactions include, Kumada coupling, Suzuki coupling, Heck coupling and Stille coupling. Kumada couplings typically use Grignard reagents as the vinyl donor group (in this case, vinyl magnesium bromide) which would be too nucleophilic for our substrate hence were ruled out. Stille couplings are known to be tolerant of functional groups but involve the use of tin-based reagents which are known for its toxicity hence were not preferred as the first choice. Suzuki couplings are generally functional group tolerant and involve the use of boron-based reagents which are less nucleophilic. These reactions are typically carried out in the presence of a base and in the mixture of organic/aqueous solvents. There was a fear that aqueous basic reaction conditions would hydrolyze the ester group on our substrate during the cross-coupling but the desired cross-coupling could be carried out in a selective manner without affecting the ester group. Even though Suzuki coupling showed promise, it was not preferred due to the cost of vinyl donor groups. The vinyl donor in Suzuki coupling, potassium salt of vinyltrifluoroborate, was expensive and hence needed to be made in-house which added more steps to the synthetic route. Instead, Heck couplings that employ silane-based reagents and quaternary ammonium salts—also known as 'Jeffery Conditions'— proved to be more promising. The vinyl source used in these couplings is vinyl trimethylsilane which is the least nucleophilic amongst other vinyl donors used in other couplings, hence providing broader substrate scope. Use of quaternary ammonium salts as phase transfer agents helps in performing these reactions at much lower temperatures (25° C.-50° C.). This was particularly useful for some of the other temperature-sensitive BCB-based substrates that are being studied in our group. Moreover, vinyl trimethylsilane is about ⅓ as expensive as vinyltrifluoroborate, making it a more attractive option. All the reagents required for this coupling are readily available commercially thereby keeping the number of synthetic steps to minimum. Other advantages include: milder reaction conditions, less toxicity of vinyl source as compared to tin-based reagents. These couplings are both cost and atom effective. These silane-based cross-couplings gave yields in the range of 40-50% to give the monomer.

In a schlenk flask, KF (1.1 gms, 19.02 mmol), n-tetrabutyl ammonium chloride (3.5 gms, 12.68 mmol) and toluene (8 ml) were stirred at room temperature to form good suspension. Molecular sieves were then added to the suspension and stirred further for 10 minutes and degassed using 2 freeze-pump-thaw cycles. The flask with degassed contents was taken in the dry box where Pd(dba)2 (547 mg, 0.95 mmol) was added, flask sealed with rubber septum on one neck and removed from drybox. In the fume hood, mixture of co-1-acetoxy-4/5-iodoBCB (1.82 gms, 6.34 mmol) and vinyl trimethylsilane (3.81 gms, 38.04 mmol) was added through the rubber septum under N2 atmosphere. Contents degassed by 2 freeze-pump-thaw cycles, backfilled with N2 and heated to 45° C. Conversion of aryl iodide was monitored by 1H NMR spectroscopy which showed complete consumption of aryl iodide after 39 hours. Reaction was stopped, diluted with Et2O, filtered over celite and filtrate reduced on rotovap. The crude was purified by multiple column chromatography iterations. First the crude was purified using 100% CH2Cl2 as eluent to obtain two fractions: (a) mixture of desired product and small amount of silylated (non-deprotected) version of the product (Rf=0.66) and (b) mixture of desired product alongwith some impurity (Rf=0.53). Each of these fractions were further purified using (a) Hexanes:Et2O (80:20) and (b) Hexanes:Et2O (70:30) as eluent system respectively to obtain the desired product in 574 mg quantity (% Yield=48%) as light yellow oil.

Polymerization of BCB Monomer

Figure 5:
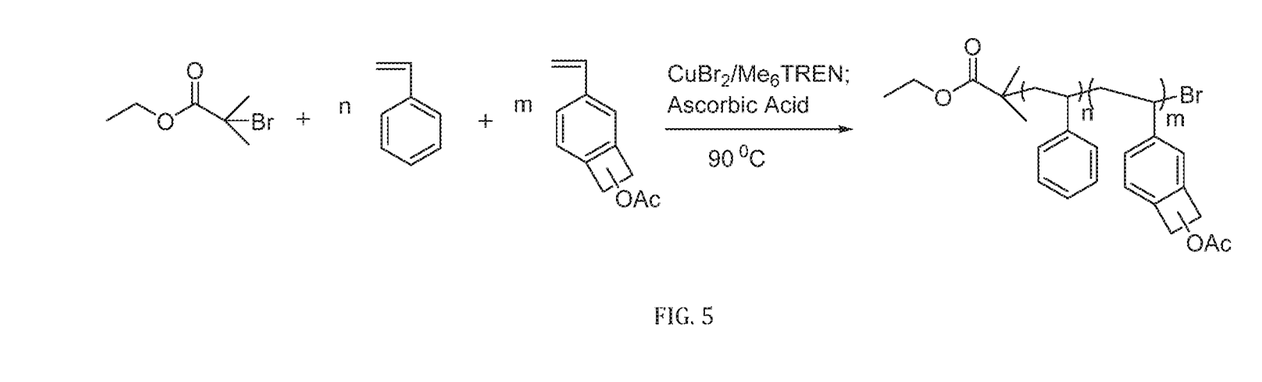
FIG. 5 shows the copolymerization of styrene with co-1-acetoxy-4/5-vinylBCB as per an experimental example provided herein.

Once this monomer was available it was evaluated for its polymerizability. Polymerization of vinyl monomers can be carried out by either ionic or radical polymerization. We decided to evaluate the polymerizability of our new monomer/crosslinker using Cu-based ATRP reaction conditions. New monomer was copolymerized with styrene using ARGET ATRP. A typical (co)polymerization using ARGET ATRP was conducted at 90° C. since it affords good compromise between the rate of polymerization and higher chain end functionality achieved at the end of the polymerization. A series of styrene (co)polymers with different molecular weights and different mol % of co-1-alkoxide-4/5-vinylBCB monomer was synthesized, as per FIG. 5 and Table 3.

TABLE 3 different copolymers with their feed ratio, composition by NMR

| Sr. No. | Feed Ratio (St:VAcOxyBCB) | Composition (St:VAcOxyBCB) ($^1$H NMR) | $M_n$ (Đ) |
| --- | --- | --- | --- |
| 1 | 95/5 | 96.5/3.5 | 31.8 kDa (Đ = 1.42) |
| 2 | 95/5 | 95/5 | 8.3 kDa (Đ = 1.29) |
| 3 | 90/10 | 90.8/9.2 | 22.8 kDa (Đ = 1.29) |
| 4 | 90/10 | | 40 kDa |

In a typical procedure, CuBr2/Me6TREN was added as a stock solution in CH3CN which was removed under vacuum. A mixture of Ethyl-2-bromoisobutyrate, styrene and co-1-acetoxy-4/5-vinylBCB was then added to CuBr2/Me6TREN and stirred at room temperature for 10 minutes. To this ascorbic acid was added, contents sealed quickly using glass stopper frozen using liq. N2. Contents were degassed by 3 freeze-pump-thaw cycles after which flask was backfilled with N2 and closed to the schlenk line and heated at 90° C. for 25 hours. Reaction was stopped by quenching the contents in liq. N2 and exposing the catalyst to atmosphere. Crude was diluted with 2 mL THF, passed over basic alumina to remove catalyst and precipitated in 40 mL MeOH to obtain white precipitate in 543 mg quantity (% Yield=35.4%). 1H NMR and GPC analysis was done.

The use of higher temperature for the polymerization of BCB containing monomers was a noticeable improvement since with our previously reported BCB monomer, 1-ethoxy vinylBCB, we were restricted to 60° C. as polymerization temperature since it was undergoing premature crosslinking above 60° C. Conducting ATRP at 60° C. in such case took a long time for the synthesis of copolymers with desired molecular weights. Moreover, the polydispersity indices obtained with this acetate substituted BCBs were less than 1-ethoxy vinylBCB. We believe that this due to the possible low chain transfer constant of acetateBCBs as compared to the ethoxyBCBs. $^1$H NMR and GPC analysis of these new copolymers indicates successful incorporation of the new monomer in the polymer with relatively narrow molecular weight distribution.

Crosslinking Reaction in the Presence of a Nucleophile

Figure 6:
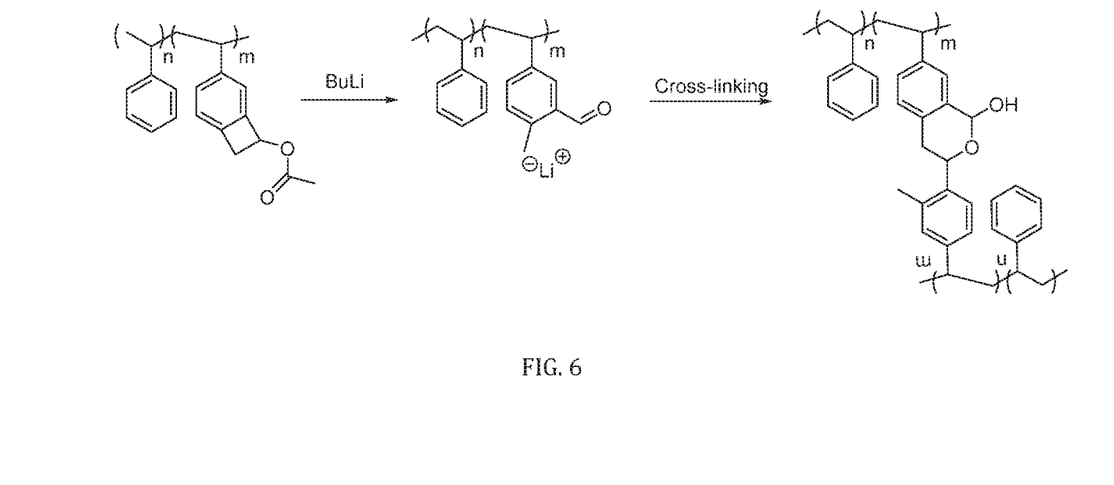
FIG. 6 shows the crosslinking of a polymer of FIG. 5 as per an experimental example provided herein.

These new copolymers were then evaluated for their ability to undergo crosslinking reaction in the presence of a nucleophile at room temperature, per FIG. 6. The procedure mentioned here is of experiment performed in drybox.

Similar experiment when performed in fume hood by carefully handling BuLi showed similar result. In a drybox, THF solution of poly(co-1-acetoxy-4/5-vinylBCB) (36 mg in 0.3 ml THF) was prepared as a clear solution. To this, an approximate excess of BuLi was added at once (2-3 drops were added; actual amount needed was 1.2 microlitres). On addition of BuLi, color of the contents instantaneously changed from colorless to dark orange the contents turned into a gel indicating instantaneous crosslinking. After 1 minute, excess of BuLi was quenched by adding 1 mL of MeOH which turned the color of the contents to light yellow. Outside the drybox, contents were concentrated on rotovap. The resulting crosslinked polymer partially dissolved in THF. THF soluble part was analyzed by GPC which showed predominantly intermolecular crosslinking.

First, we attempted to crosslink acetoxyBCB containing copolymers under 'concentrated' conditions using BuLi as the nucleophile at room temperature (FIG. 6). BuLi was added at once over THF solution of poly(styrene-co-1-acetoxy-4/5-vinylBCB) [concentration of BCB in the solution=0.33 M] which resulted in instantaneous color change of the solution and gelling of the solution indicating rapid deprotection of the acetate group and subsequent crosslinking at room temperature. Reaction of BuLi with styrene under such reaction conditions is unlikely. Excess of BuLi and alkoxides formed in the reaction were quenched within a minute of addition of nucleophile. Analysis of the resulting product by GPC showed that indeed the copolymer was crosslinked as higher molecular weight species could be detected (FIG. 1). Using these 'concentrated' conditions, it formed intramolecular as well as intermolecular crosslinking. Also, $^1$H NMR showed complete disappearance of the resonances belonging to methine and methylene protons of 1-acetoxyBCB indicating complete deprotection of the acetate group. The results proved our hypothesis that alkoxideBCB containing polymers can be rapidly crosslinked at room temperature. This is a significant improvement in the field of BCB-containing polymer crosslinking since typical temperatures required for crosslinking were always higher (>200° C. in the case of unsubstituted BCB and >140° C. in case of ether substituted BCB which is a recent development). Our new crosslinker reduces the temperature required for crosslinking by approximately one order of magnitude although by chemical activation of BCBs. Nucleophile activation of 1-acetoxyBCB containing polymer to obtain crosslinked polymer can also be looked at as a 2-component crosslinking/curing system similar to the classical 2-component epoxy-amine system but with much faster rates of crosslinking at room temperature.

This NaOMe mediated instantaneous crosslinking can be applied to polymers other than polystyrenes, such as PMMA.

Since we observed rapid crosslinking of 1-alkoxideBCB containing polymers at room temperature, it is noted that there can also be crosslinking at sub-ambient temperatures since it is possible that the rate of deprotection followed by crosslinking could still be higher at sub-ambient temperatures.

Single Chain Polymer Nanoparticles—Intramolecular Crosslinking

New findings of our research regarding rapid room temperature crosslinking of 1-alkoxideBCB containing polymers were then utilized to make Single Chain Polymer Nanoparticles (SCPNs). SCPNs are increasingly gaining attention as nanostructures in the sub-20 nm size range for their potential applications in various fields. As the name suggests, SCPNs are nanoparticles made out of a single polymer chain via selective intramolecular crosslinking forming (non)covalent bonds between the units of same chain. In the last decade, a wide range of chemistries have been employed towards the synthesis of these nanoparticles, e.g., radical, click, photo, thermal, etc. Even though varying chemistries were used, most of the reports utilize 'ultra-high dilution method' in order to achieve selective intramolecular crosslinking over intermolecular crosslinking. This method typically requires a large excess of solvent since to keep the concentration of polymer low enough for selective intramolecular crosslinking [typical concentration of polymer is around $10^{-6}$ M]. The other method called as 'pseudo high dilution continuous addition method' utilizes much less solvent and relies on rapid crosslinking reaction conditions [typical concentration of polymer is around $10^{-2}$-$10^{-4}$ M] to achieve selective intramolecular crosslinking. The latter method that uses at least two orders of magnitude concentrated solution has clear advantage since it uses much less solvent. Despite this advantage, only few reports, such as Harth, E. et al.; *J. Am. Chem. Soc.* 2002, 124, 8653-8660 and Croce, T. A. et al.; *Macromolecules* 2007, 40, 6028-6031 utilize pseudo-high dilution method. This is mainly because not all the chemistries employed for the synthesis of SCPNs are 'rapid' enough, a key requirement for the use of pseudo-high dilution method. As mentioned earlier, our new monomer/crosslinker gave access to BCB containing polymers that could be crosslinked rapidly at room temperature. We decided to utilize this unique chemistry to make SCPNs using pseudo-high dilution method at room temperature.

The reaction is shown in FIG. 6. The procedure mentioned here is of experiment partially performed in drybox. Similar experiment when performed in fume hood by carefully handling BuLi showed similar result. In dry box benzene solution of copolymer (50 mg in 12 mL benzene) was prepared and transferred to a plastic syringe. Also, BuLi solution in benzene (0.12 mL BuLi in 50 mL benzene) was prepared in drybox and transferred to 3-neck round bottom flask and setup was sealed. In the fume hood, copolymer solution was added to BuLi solution in benzene under N2 using syringe pump at the rate of 1.0 ml/hour at room temperature. On complete addition of BuLi color of the contents was colorless and was stirred for additional 30 minutes. Excess of BuLi was then quenched by adding 1 mL of MeOH and 1 mL of saturated aqueous ammonium chloride solution. Solids were formed (presumably LiOMe) and were filtered and disposed. Filtrate was reduced on rotovap, redissolved in 3 mL of THF and precipitated in 50 mL of cold MeOH to obtain white powder. NMR showed complete consumption of BCB and GPC showed selective intramolecular crosslinking In a typical experiment, a concentrated solution of poly(styrene-co-1-acetoxy-4/5-vinylBCB) in benzene [concentration of BCB in the solution=0.01 M] was added continuously over a solution of BuLi in benzene using syringe pump (rate of addition=1 ml/hr). On complete addition, contents were quenched and analyzed by GPC and $^1$H NMR. GPC showed reduced apparent molecular weight of the crosslinked nanoparticle compared to the linear polymer precursor and did not show any higher molecular weight species indicating selective intramolecular crosslinking. $^1$H NMR showed complete disappearance of characteristic resonances belonging to 1-acetoxyBCB indicating that the crosslinking occurred through acetoxyBCB. TEM analysis showed formation of globular nanostructures in the size range of 10-20 nm; which is consistent with the sizes reported in the literature for SCPNs. Even though SCPNs have been made previously at room temperature, relatively slower chemis- tries were employed making it necessary to use ultra-high dilution method. In contrast, our method uses concentrated solution to obtain SCPNs at room temperature.

In summary, we have reported the synthesis of a new monomer/crosslinker based on 1-acetoxyBCB. Once incorporated in the polymer backbone, this crosslinker could be activated by a nucleophile to obtain crosslinked material via rapid crosslinking reaction at ambient and even sub-ambient temperatures. To the best of our knowledge this is the first example of rapid polymer crosslinking at ambient/sub-ambient temperatures. We believe that the broader comonomer scope available with this new crosslinker coupled with lower temperature requirement will qualify it for potential applications in more fields.

In light of the foregoing, it should be appreciated that the present invention significantly advances the art by providing benzocyclobutene monomers and uses thereof that are structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A method of forming a copolymer comprising the steps of:
copolymerizing a first monomer and a second monomer, the second monomer being selected according to the following chemical formula:

wherein R1 is selected from the group consisting of:

wherein n is 0 or more; or R1 is non-existent, or wherein Z is any linkage between the norbornene and the benzene ring; wherein R2 is selected from CH3, aliphatic groups, cycloaliphatic groups, and aromatic groups, wherein A is either non-existent or is selected from any structural unit that is incapable of reacting with a nucleophile, and crosslinking the resultant copolymer at a temperature from 15.5° C. to 35° C.

2. The method of claim 1 wherein the first monomer is selected from the group consisting of styrene, acrylates, methacrylates, acrylamides, methacrylamides, cyclopentenes, norbornenes, and cyclooctadienes.

3. The method of claim 1 wherein R1 is HC=CH2, and copolymerization is carried out through radical polymerization.

4. The method of claim 1 wherein R1 is:

and copolymerization is carried out through radical polymerization.

5. The method of claim 1 wherein R1 is and copolymerization is carried out through radical polymerization.

6. The method of claim 1 wherein R1 is and copolymerization is carried out through ring-opening metathesis.

7. The method of claim 1 wherein said step of crosslinking occurs in the presence of a nucleophile, wherein the nucleophile is selected from the group consisting of BuLi, sec-BuLi, NaOMe, nBuNa, and LiOMe.

8. The method of claim 7 wherein the crosslinking is intermolecular crosslinking.

9. The method of claim 7 wherein the crosslinking is intramolecular crosslinking.

10. The method of claim 1 wherein the second monomer has the formula:

* * * * *